United States Patent [19]

Leopold

[11] 4,255,419

[45] Mar. 10, 1981

[54] ZINC DEFICIENCY IN MULTIPLE SCLEROSIS

[75] Inventor: Irving H. Leopold, Newport Beach, Calif.

[73] Assignee: Allergan Pharmaceuticals, Inc., Irvine, Calif.

[21] Appl. No.: 79,266

[22] Filed: Sep. 27, 1979

[51] Int. Cl.³ .............................................. A61K 33/30
[52] U.S. Cl. ..................................................... 424/145
[58] Field of Search ........................................ 424/145

[56] References Cited

PUBLICATIONS

*The Merck Manual,* 12th Ed. (1972), pp. 1333–1342, Merck & Co., Rahway, N.J.

*Primary Examiner*—Frederick E. Waddell
*Attorney, Agent, or Firm*—Martin A. Voet

[57] ABSTRACT

Low serum zinc concentrations in humans have been associated with multiple sclerosis in some patients, particularly those patients under 50 years of age. Increasing the concentration of serum zinc in such patients has been found to lower the number of, or decrease the severity of recurrent attacks and/or improve neurologic function in some patients.

6 Claims, No Drawings

ZINC DEFICIENCY IN MULTIPLE SCLEROSIS

BACKGROUND OF THE INVENTION

1. Field of the Invention

The invention relates to a method of treatment of a disease process in humans. More particularly, the invention relates to a method of treatment of humans having multiple sclerosis.

2. Background of the Prior Art

While zinc has heretofor been referred to as a trace element in human nutrition, in reality its concentration in humans is second only to that of iron in the metals. The body of a 70 kg adult contains between 1.4 and 2.3 grams of zinc, about one-half of the amount of iron.

Zinc is found in highest concentrations in the prostate, blood, skin, hair, liver and eyes of man. Seventy-five to eighty percent of the zinc in the blood is associated with the enzyme, carbonic anhydrase in the erythrocytes. Human serum normally contains 98-142 micrograms of zinc per deciliter. Significant quantities of zinc are also found in the muscles, brain, kidneys and spleen. The average adult human normally loses about 2-3 mg of zinc per day. Gastrointestinal losses account for approximately one-half of this total, with the remainder being lost in the urine and sweat. In young men, deficiency causes stunted growth, anemia (from concomitant iron deficiency), enlarged liver and spleen and underdevelopment of genitals and secondary sex characteristics. Deficiency of zinc may be caused by the nature of the diet (high in phytic acid), by the excretion of zinc in perspiration, or by blood loss if there is parasitic infection. In animals, zinc deficiency causes hyperirritability, anorexia, retardation of growth, loss of hair and changes in the skin and sometimes in the cornea.

Zinc is a constituent of several vitally important enzymes in addition to carbonic anhydrase, including carboxypeptidase, alkaline phosphatase, lactic acid and alcohol dehydrogenases. The last named enzymes occur in the eye, and indeed, the eye contains a considerable amount of this metal, as do the testes and the teeth. Zinc seems to be present in the pancreas, and it accompanies insulin when this hormone is crystallized. Diabetic pancreatic tissue contains only half as much zinc as does normal tissue. Zinc is present in the insulin molecule but is not essential to the activity of insulin. Other investigators have claimed that zinc is localized in the α-cells of the pancreas and have suggested that it is related more to glucagon content than to insulin. There is current evidence indicating that low levels of zinc intake are associated with impairment of the acuity of the senses of taste and smell.

There is increasing evidence that zinc plays an important role in protein biosynthesis and utilization. The addition of small amounts of zinc to a diet containing sub-optimal amounts of a vegetable protein, as indicated by the growth of young rats, causes a pronounced increase in protein utilization and growth. This defect may result from a failure in adequate RNA synthesis. Zinc apparently inhibits the enzyme ribonuclease. Thus, in zinc deficiency, excessive destruction of RNA could occur, which might result in the defects of protein synthesis seen in zinc deficiency as well as the other sequelae observed.

The adult human being ingests from 12 to 20 mg of zinc per day. Although this element is widely distributed, the high content of phytate in certain foods may limit its absorption and result in a deficiency with the clinical symptoms described above. The recommended daily dietary allowance for zinc for the adult is 15 mg, with 20 and 25 mg during pregnancy and lactation, respectively, comparable to the recommended daily dietary allowance for iron.

Ingestion of excessive amounts of zinc leads to vomiting, dehydration, lack of muscle coordination, dizziness and electrolyte imbalances. A 2 gm dose of oral zinc sulfate has been used as an emetic. The lethal dose of zinc sulfate is not known, but it is estimated to be on the order of 15 grams, though it should be noted that zinc is not accumulated by the body.

Zinc has heretofore been used or suggested for use in a number of therapeutic applications, including treatment of *acrodermatitis enteropathica,* acne and in wound healing, see for example, "Therapeutic Uses of Oral Zinc," *U.S. Pharmacist,* P. 61, April 1979.

Although the exact structure of phytates are not known, phytates are insoluble, mixed calcium and magnesium salts of phytic acid, which in turn is a hexaphosphate of inositol. Available evidence indicates that phytic acid and its compounds interfere with the absorption of calcium, zinc and iron from the intestinal tract. Unrefined cereals are rich in phytates, but white flour contains little. Hence the phytate problem is not serious in the United States; but in areas of the world where unrefined cereals form a large part of the diet and little calcium is consumed, the interference with calcium absorption may result in serious deficiencies of calcium, including the development of so-called "cereal rickets".

Multiple sclerosis (MS) is a disease marked by scleroses occurring in sporadic patches throughout the brain or spinal cord, or both. Among its symptoms are weakness, incoordination, strong jerking movements of the legs and especially of the arms, amenomania or other abnormal mental exaltation, scanning speech, nystagmus, etc.

In the past 100 years, numerous seemingly unrelated clues have been discovered regarding the pathogenesis and etiology of MS. Epidemiologic reports suggest that the geographical distribution of MS primarily affects inland areas, occurring infrequently in seacoast towns. The disease is rare in the Orient. If immigration occurs before the age of 15 years and patients are reared in a foreign country from early childhood, they develop the incidence of MS of the country to which they have immigrated. The patient who immigrates after 15 years of age will have the incidence of MS of his parent country. The question of an infectious agent such as a virus, has been entertained as an etiology for MS. This disease has never been shown to pass from one animal to another, yet epidemics of MS have been reported. After the age of 50, the incidence of MS is quite low.

SUMMARY OF THE INVENTION

It has now been discovered that low levels of serum zinc in humans under the age of 50 may be associated with multiple sclerosis in some patients having MS. Furthermore, it has been discovered that some symptoms of the disease may be reduced or eliminated in some patients having the disease and, especially in patients under the age of 35, by elevating the serum zinc to normal levels.

Elevation of serum zinc to normal levels may be accomplished in a number of ways; the simplest and most convenient in most cases being by ingestion of an edible non-toxic amount of zinc-containing material, e.g., a dietary zinc supplement such as zinc sulfate, in sufficient quantities to elevate the serum zinc to normal levels. Alternate means include removing or inactivating substances in the body which, if present, tend to reduce normal serum zinc levels, e.g., phytates or other zinc ligands, or by systemic administration, e.g., intravenous injection, of a slow-release form of zinc, e.g., zinc chelated with dextrose or other suitable chelating agent.

More specifically, the invention relates to a method of treating multiple sclerosis in a human having multiple sclerosis and having lower than normal concentrations of serum zinc comprising elevating the serum zinc level in said human.

The invention further relates to a method of treating multiple sclerosis in a human having multiple sclerosis and having lower than normal concentrations of serum zinc comprising elevating the serum zinc concentration in said human by oral administration to said human of an effective, non-toxic, zinc serum-elevating amount of zinc sulfate.

DETAILED DESCRIPTION OF THE INVENTION

As used herein, the term "method of treating multiple sclerosis" means a method of temporarily alleviating or reducing one or more of the symptoms of multiple sclerosis or temporarily improving neurologic function in a patient having multiple sclerosis.

As used herein, the term "ingestible zinc" refers to non-toxic zinc-containing compounds and complexes which may be assimilated by the body upon oral administration. Examples of ingestible zinc include zinc carbonate, zinc sulfate, zinc aspartate, zinc gluconate, zinc citrate, zinc tartrate, zinc glycerol phosphate, zinc lactate and preferably zinc sulfate.

As used herein, the term "effective amount" means that amount of ingestible zinc which is necessary to elevate the serum zinc concentration to approximately normal levels or higher. The exact amount which may be prescribed will vary with the size, weight and sex of the patient, his or her serum zinc level and his or her ability to tolerate and assimilate zinc. Generally, amounts of 10-1,000 mg of zinc per day may be used and preferably 50-500 mg per day of a suitable zinc supplement, administered orally.

EXAMPLE I

The serum zinc concentrations of 26 multiple sclerosis patients were compared with the serum zinc concentrations of an age and sex-matched group of 39 persons with no known cause for zinc deficiency (control).

The serum zinc levels were determined from blood plasma samples with a flameless atomic absorption spectrophotometer. The concentration of zinc in the plasma was determined from a calibration curve using aqueous zinc standard solutions. At least three determinations were made on each diluted plasma sample.

The results are shown in Tables 1 and 2 below:

TABLE 1

|  | MS Patients | | | Control Group | | |
| --- | --- | --- | --- | --- | --- | --- |
|  | Total Sample | $<50$ Years | $\geq 50$ Years | Total Sample | $<50$ Years | $\geq 50$ Years |
| # Patients | 26 | 20 | 6 | 39 | 27 | 12 |
| Mean Age (Years) | 44 | 39 | 65 | 37 | 30 | 55 |
| Mean Zinc (PPb) | 755 ± 92 | 759 ± 99 | 740 ± 69 | 882 ± 162 | 899 ± 181 | 843 ± 105 |

TABLE 2

| Statistical Analysis of Data of Table 1 | | |
| --- | --- | --- |
|  | Control Group vs MS Patients | |
|  | $<50$ Years | $\geq 50$ Years |
| Degrees of Freedom | 44 | 16 |
| t | 3.61 | 0.144 |
| Levels of Significance (P) | $<0.001$ | $<0.65$ |

In comparing the control group to multiple sclerosis patients according to age and zinc levels, one sees that before the age of 50, the two groups appear as two distinct populations with a statistical confidence level of $P<0.001$, a high level of confidence. When looking at the two populations for patients 50 years of age or older, the two populations become indistinguishable with a statistical confidence level of $P<0.65$.

Furthermore, the MS patients do not show a significant change in their zinc level even after age 50, while the normal population shows a significant decrease in zinc level with increasing age. Since the zinc level of MS patients does not decrease with age, there is a point at which the normals and the MS patients will have comparable zinc levels.

Clinically, it is known that after the age of 50, the number of attacks to multiple sclerosis patients diminish considerably and the new cases are extremely rare after the age of 50. As the difference in the serum zinc level between the control group and MS patients becomes negligible after age 50, so too does the incidence of multiple sclerosis. Thus, there seems to be a positive relationship between serum zinc deficiency and incidence of multiple sclerosis.

EXAMPLE II

Fourteen of the multiple sclerosis patients from the study in Example I were treated with one 220 mg tablet of zinc sulfate per day for 8 weeks. All of the patients showed significant elevations of serum zinc within one to two weeks. The results of the study are shown in Table 3 on the next page:

TABLE 3

| Multiple Sclerosis Patients on Zinc Supplement | | | |
| --- | --- | --- | --- |
| # of Patients (%) | Improved 7 (50%) | No Change 5 (35.7%) | Worse 2 (14.3%) |
| Age (Sex) | 33 (m)  32 (f) | 63 (f)  30 (m) | 48 (m) |
|  | 25 (f)  45 (f) | 46 (m)  66 (f) | 42 (f) |
|  | 32 (f)  48 (f) | 67 (f) |  |
|  | 32 (f) |  |  |
| Average Age (Yrs) | 35 | 54 | 45 |

Table 3 indicates that 7 of 14 patients showed some type of improvement in neurologic function after serum zinc levels were increased. The average age of patients who showed improvement was 35, while the average age of patients who had no change or got worse was 52. This finding is consistent with the results of Example I which showed no significant difference in the serum zinc levels between multiple sclerosis patients and normal patients 50 years of age or older.

I claim:

1. A method of treating multiple sclerosis in a human having multiple sclerosis and having lower than normal concentrations of serum zinc comprising elevating the serum zinc level in said human.

2. A method of treating multiple sclerosis in a human having multiple sclerosis and having lower than normal concentrations of serum zinc comprising elevating the serum zinc concentration in said human by oral administration to said human of an effective, non-toxic zinc serum-elevating amount of ingestible zinc.

3. The method of claim 2, wherein said ingestible zinc is a non-toxic zinc salt.

4. The method of claim 3, wherein said zinc salt is selected from the group consisting of zinc sulfate and zinc carbonate.

5. A method of treating multiple sclerosis in a human having multiple sclerosis and having lower than normal concentrations of serum zinc comprising elevating the serum zinc concentration in said human by oral administration to said human of an effective, non-toxic zinc serum-elevating amount of zinc sulfate.

6. The method of claim 5, wherein an effective amount is approximately 50–500 mg per day.

* * * * *